(12) United States Patent
Cotter et al.

(10) Patent No.: US 6,346,535 B1
(45) Date of Patent: Feb. 12, 2002

(54) FUNGICIDAL MIXTURES

(75) Inventors: Henry Van Tuyl Cotter, Trenton, NJ (US); Gunther Reichert, Bubenheim; Ewald Sieverding, St. Johann, both of (DE); Petrus Martinus Franciscus Emanuel Jegerings, Wavre (BE)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/240,412

(22) Filed: Jan. 29, 1999

(51) Int. Cl.$^7$ .................. A01N 43/54; A01N 37/12; A01N 37/44; A01N 37/02; A01N 35/00
(52) U.S. Cl. ............... 514/269; 514/538; 514/539; 514/546; 514/552; 514/687
(58) Field of Search ............... 514/538, 687, 514/539, 269, 546, 552

(56) References Cited

U.S. PATENT DOCUMENTS 5,922,905 A   7/1999   Curtze et al. ............. 562/474
5,945,567 A   8/1999   Curtze et al. ............. 568/333

OTHER PUBLICATIONS

Tomlin, The Pesticide Manual, eleventh edition(1997), pp. 70–72, 743 and 744.*

* cited by examiner

Primary Examiner—Allen J. Robinson
(74) Attorney, Agent, or Firm—Charles F. Costello

(57) ABSTRACT

The invention relates to a novel fungicidal composition comprising synergistically effective amounts of at least one benzophenone of formula I

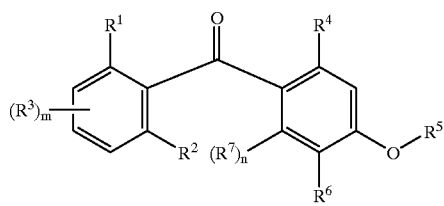

wherein
$R^1$ represents a halogen atom, an optionally substituted alkyl, alkanoyloxy or alkoxy group; or a hydroxy group,
$R^2$ represents a halogen atom or an optionally substituted alkyl group,
$R^3$ independently represents a halogen atom, an optionally substituted alkyl or alkoxy group or a nitro group;
m is 0 or an integer of 1 to 3;
$R^4$ represents a halogen atom, a cyano, carboxy, hydroxy or nitro group or an optionally substituted alkyl, alkoxy, alkenyl, alkylthio, alkylsulphinyl, alkylsulphonyl or amino group;
$R^5$ represents an optionally substituted alkyl group;
$R^6$ represents a halogen atom or a nitro group, an optionally substituted alkyl, alkoxy, alkenyloxy, alkynyloxy, alkylthio, cycloalkyl, cycloalkyloxy, aryloxy group;
$R^7$ independently represents a halogen atom, an optionally substituted alkyl, alkenyl, alkynyl, alkoxy, alkenyloxy, alkynyloxy, cycloalkyl, cycloalkoxy group;
n is 0 or 1; and
at least one fungicidally active ingredient selected from the groups consisting of (A), (B), (C), (D) and (E) wherein:
(A) is an ergosterol biosynthesis inhibitor;
(B) is a strobilurine derivative,
(C) is a melanin biosynthesis inhibitor;
(D) is a compound selected from the group consisting of acibenzolar, benomyl, captan, carboxin, chlorothalonil, copper, cyprodinil, dinocap, dithianon, dimethomorph, dodine, ethirimol, famoxadone, fenpiclonil, fluazinam, mancozeb, metalaxyl, pyrifenox, sulfur, vinclozolin and
(E) is an azolopyrimidine of formula II

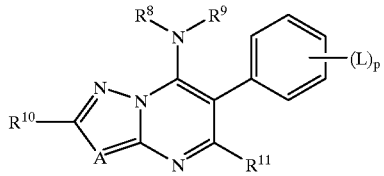

wherein
$R^8$ and $R^9$ each independently represent hydrogen or an optionally substituted alkyl, alkenyl, alkynyl, alkadienyl, aryl, heteroaryl, cycloalkyl, bicycloalkyl or heterocyclyl group, or
$R^8$ and $R^9$ together with the interjacent nitrogen atom represent an optionally substituted heterocyclic ring,
$R^{10}$ represents hydrogen or an alkyl or aryl group,
$R^{11}$ represents a hydrogen or halogen atom or an alkyl or alkoxy group,
L independently represents a halogen atom or an optionally substituted alkyl or alkoxy group,
p is 0 or an integer from 1 to 5; and
A represents N or $CR^2$, wherein $R^{12}$ has the meaning given for $R^{10}$;
together with a fungicidally acceptable carrier and/or surface active agent, and to a method of controlling the growth of phytopathogenic fungi which comprises applying synergistically effective amounts of the composition to the locus.

7 Claims, No Drawings

FUNGICIDAL MIXTURES

BACKGROUND OF THE INVENTION

The present invention relates to a fungicidal composition comprising a fungicidally acceptable carrier and/or surface active agent and synergistically effective amounts of (a) at least one benzophenone of formula I

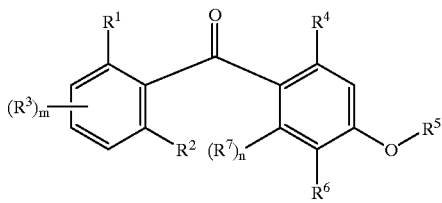

(I)

wherein $R^1$ represents a halogen atom, an optionally substituted alkyl, alkanoyloxy or alkoxy group; or a hydroxy group, $R^2$ represents a halogen atom or an optionally substituted alkyl group, $R^3$ independently represents a halogen atom, an optionally substituted alkyl or alkoxy group or a nitro group;

m is 0 or an integer of 1 to 3;

$R^4$ represents a halogen atom, a cyano, carboxy, hydroxy or nitro group or an optionally substituted alkyl, alkoxy, alkenyl, alkylthio, alkylsulphinyl, alkylsulphonyl or amino group;

$R^5$ represents an optionally substituted alkyl group;

$R^6$ represents a halogen atom or a nitro group, an optionally substituted alkyl, alkoxy, alkenyloxy, alkynyloxy, alkylthio, cycloalkyl, cycloalkyloxy, aryloxy group;

$R^7$ independently represents a halogen atom, an optionally substituted alkyl, alkenyl, alkynyl, alkoxy, alkenyloxy, alkynyloxy, cycloalkyl, cycloalkoxy group;

n is 0 or 1; and (b) at least one fungicidally active ingredient selected from the group consisting of (A), (B), (C), (D) and (E) wherein (A) is an ergosterol biosynthesis inhibitor;

(B) is a strobilurine derivative, (C) is a melanin biosynthesis inhibitor, (D) is a compound selected from the group consisting of acibenzolar, benomyl, captan, carboxin, chlorothalonil, copper, cyprodinil, dinocap, dithianon, dimethomorph, dodine, ethirimol, famoxadone, fenpiclonil, fluazinam, mancozeb, metalaxyl, pyrifenox, sulfur and vinclozolin, and (E) is an azolopyrimidine of formula II

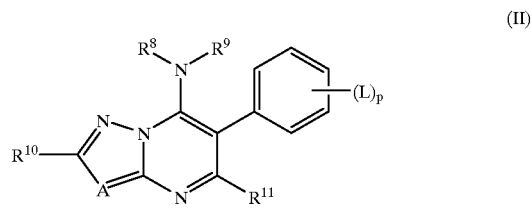

(II)

wherein $R^8$ and $R^9$ each independently represent hydrogen or an optionally substituted alkyl, alkenyl, alkynyl, alkadienyl, aryl, heteroaryl, cycloalkyl, bicycloalkyl or heterocyclyl group, or $R^8$ and $R^9$ together with the interjacent nitrogen atom represent an optionally substituted heterocyclic ring, $R^{10}$ represents hydrogen or an alkyl or aryl group, $R^{11}$ represents a hydrogen or halogen atom or an alkyl or alkoxy group, L independently represents a halogen atom or an optionally substituted alkyl or alkoxy group, p is 0 or an integer from 1 to 5; and A represents N or $CR^{12}$, wherein $R^{12}$ has the meaning given for $R^{10}$.

The fungicidal compounds of formula I utilized in the present invention are disclosed in U.S. Pat. No. 5,773,663.

The compounds of the classes (A), (B) and (D) are disclosed in The Pesticide Manual $11^{th}$ edition 1997, edited by C. Tomlin (British Crop Protection Council).

The class of melanin biosynthesis inhibitors (MBI) (C) are chemical compounds which are capable of diminishing the in vivo synthesis of melanin by inhibiting any of the reductase and/or dehydratase enzymes which are responsible for converting tetrahydroxynaphthalene into dihydroxynaphthalene. This class of compounds includes the following known compounds: carpropamid, chlobenthiazione, diclocymet, pyroquilon, phthalide, tricyclazole and certain phenoxyamides, in particular AC 382042, which are discussed, for example, in EP 0 262 393, and Japanese patent application JP 5-9165-A.

The fungicidal compounds of formula II utilized in the present invention are disclosed in U.S. Pat. No. 5,593,996 and International Patent Applications WO 98/46607 and WO 98146608.

U.S. Pat. No. 5,773,663 suggests combinations of fungicidal benzophenone derivatives with other fungicides such as 4,6-dinitro-o-cresol, benalaxyl, benomyl, captafol, captan, carbendazim, chlorothalonil, copper, cymoxanil, dichlofluanid, dichlone, difenoconazole, dimethomorph, diniconzole, dinocap, dithianon, fenpiclonil, fenpropiomorph, hymaxazol, imazalil, iprodione, isoprothiolane, kasugamycin, mancozeb, mepronil, mercuric oxide, oxadixyl, oxolinic acid, penconazole, propineb, pyrifenox, thiabendazole, thiram, tolclofos-methyl, triadimefon, triflumizole, triforine validamycin A, vinclozolin, zineb and ziram.

However, there is no suggestion that such mixtures show synergistic effects and can advantageously be used for controlling diseases such as wheat powdery mildew, wheat leaf rust and wheat Septoria leaf blotch, Botrytis diseases and others.

Surprisingly, a strong synergy between the compounds of formula I and the fungicidally active ingredients selected from the classes (A), (B), (C), (D) and (E) as described above in greenhouse and field trials was found when these two compounds were in-tank mixed and when the activity of these mixtures was compared with that of the solo activity of each active ingredient.

A mixture of fungicides shows synergistic effect if the actual (observed) fungicidal activity from the mixture is greater than the expected activity based on the activities when each fungicide is applied separately. A standard method for calculating the expected fungicidal activity for a given mixture of two fungicides is as follows:

$$EE = x + y - x \cdot y / 100$$

wherein x is the efficacy in % compared with an untreated control upon treatment with a fungicidal active ingredient A at a dose rate a;

y is the efficacy in % compared with an untreated control upon treatment with a fungicidal active ingredient B at a dose rate b;

EE is the expected efficacy with a combination of fungicidal active ingredients A and B at a dose of a+b, respectively.

If the actual efficacy (E) exceeds the expected (calculated) one (EE), the mixture displays a synergistic effect.

SUMMARY OF THE INVENTION

The present invention includes a fungicidal composition comprising an acceptable carrier and/or surface active agent and synergistically effective amounts of at least one compound of formula I, and at least one fungicidal active ingredient selected from the group consisting of (A), (B), (C), (D) and (E) wherein (A) is an ergosterol biosynthesis inhibitor;

(B) is a strobilurine derivative, (C) is a melanin biosynthesis inhibitor, (D) is a compound selected from the group consisting of acibenzolar (BION), benomyl, captan, carboxin, chlorothalonil, copper, cyprodinil, dinocap, dithianon, dimethomorph, dodine, ethirimol, famoxadone, fenpiclonil, fluazinam, mancozeb, metalaxyl, pyrifenox, sulfur and vinclozolin, and (E) is an azolopyrimidine of formula II.

The present invention also includes a method of controlling the growth of phytopathogenic fungi at a locus which comprises applying to the locus synergistically effective amounts of at least one benzophenone of formula I and at least one fungicidally active ingredient selected from the group consisting of (A), (B), (C), (D) and (E) as defined above.

DETAILED DESCRIPTION OF THE PREFERRED EMBODIMENTS

Preferred compounds of formula I for use in the compositions and methods of the present invention are the benzophenones of formula IA,

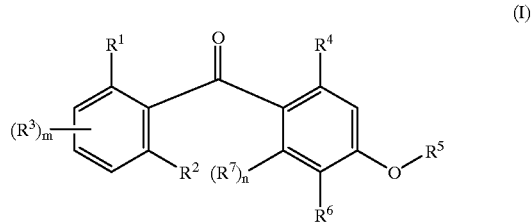

wherein $R^1$ represents a halogen atom, a methyl, trifluoromethyl, methoxy or hydroxy group, in particular, a chlorine atom, a methyl or methoxy group;

$R^2$ represents a halogen atom, in particular, a chlorine atom or a methyl group;

$R^3$ represents a bromine or chlorine atom, a methyl, trifluoromethyl or nitro group, in particular, a bromine atom;

n is 0 or 1

$R^4$ represents a methyl group;

$R^5$ represents an alkyl group, in particular, a methyl group; and $R^6$ and $R^7$ each independently represent an alkoxy group which may be substituted by a phenyl, alkylphenyl or halophenyl group, preferably C1–6 alkoxy being optionally substituted by a phenyl, methylphenyl or fluorophenyl group, in particular methoxy, benzyloxy and 2-fluorobenzyloxy.

Particularly preferred are the benzophenones selected from the group consisting of 6'-butoxy-2,6-dichloro-4',5'-dimethoxy-2'-methylbenzophenone (hereinafter coded BP-1), 2,6-dichloro-4',5'-dimethoxy-6'-(2-fluorobenzyloxy)-2'-methylbenzophenone (hereinafter coded BP-2), 6'-benzyloxy-4,5'-dimethoxy-2,6-dimethyl-2'-methylbenzophenone (hereinafter coded BP-3); 5-bromo-2', 6-dimethyl-2,4',5',6'-tetramethoxybenzophenone (hereinafter coded BP-4) and 2,6-dichloro-2'-methyl-4',5',6'-trimethoxybenzophenone (hereinafter coded BP-5), of these, most preferred is BP-4.

The ergosterol biosynthesis inhibitors of (A) are well-known fungicidally active compounds described in, for instance, The Pesticide Manual 11th edition edited by C. Tomlin (British Crop Protection Council). Preferred ergosterol biosynthesis inhibitors include fenarimol, fenpropimorph, fenpropidine, spiroxamine and triforine.

Another preferred group of ergosterol biosynthesis inhibitors are azole derivatives of formulae IIIA and IIIB,

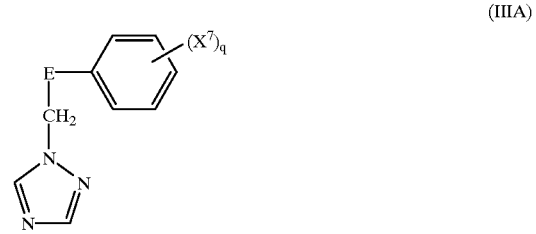

wherein

E represents a linking group selected from the groups (a), (b), (c), (d) and (e):

(a)

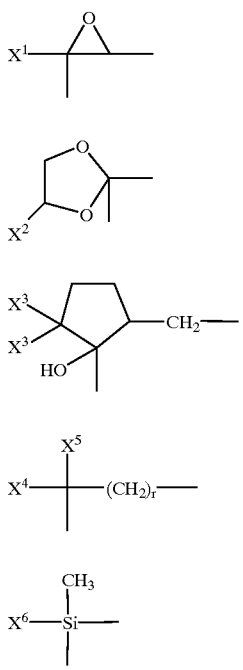

(b)

(c)

(d)

(e)

in which
X¹ represents an alkyl or an optionally substituted phenyl group;
X² and X³ each independently represent a hydrogen atom or an alkyl group;
X⁴ represents an alkyl or cyclopropylalkyl group;
X⁵ represents a hydroxy or cyano group;
X⁶ represents an optionally substituted phenyl group;
X⁷ represents a halogen atom;
q is 1, 2 or 3; and
r is 0 or 2;

(IIIB)

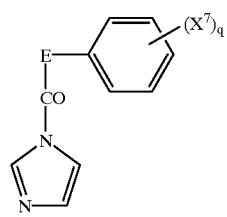

wherein X⁷ and q have the meaning given for formula IIIA, and E represents a group of the formula —N(X⁸)—(CH₂)ₛ—O—, in which X⁸ represents a hydrogen atom or an alkyl group and s is an integer from 1 to 6.

Particularly preferred azole derivatives of (A) are cyproconazole, epoxiconazole, flusilazole, metconazole, myclobutanil, penconazole, prochloraz, propiconazole, tebuconazole, triadimefon and tridimenol. Most preferred are epoxiconazole, metconazole, myclobutanil and prochloraz.

The term "strobilurine" as utilized herein includes synthetic analogues of the natural lead molecule strobilurine A, which is an antifungal secondary metabolite of the agaric *Strobilus tenacellus*. They are capable of inhibiting the mitochondrial respiration by blocking electron transfer at the bc1-complex in fungi.

Preferred strobilurine derivatives of (B) are the compounds of formula IV, (IV)

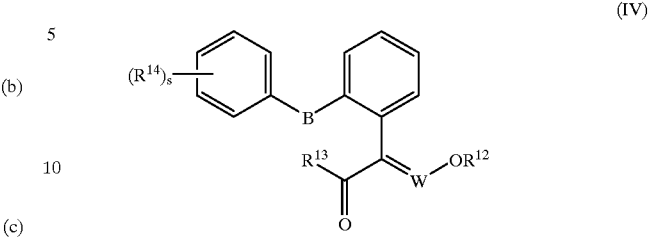

wherein
W represents N or CH;
B represents a —O—, —OCH₂—, a —CH₂O—, a pyrimid-4,6-dioxydiyl group or a group of the formula

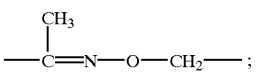

$R^{12}$ represents a $C_{1-4}$ alkyl group;
$R^{13}$ represents a $C_{1-6}$ alkoxy or a $C_{1-6}$ alkylamino group;
$R^{14}$ represents a hydrogen or halogen atom or a cyano, a $C_{1-4}$ alkyl or a
$C_{1-4}$ haloalkyl group; and
s is 0, 1 or 2.

Particularly preferred formula IV strobilurine derivatives are azoxystrobin, kresoxim methyl, trifloxystrobin or SSF126, and most preferred are azoxystrobin and kresoxim methyl.

Preferred melanin inhibitors of (C) are capropamid, chlobenthiazone, diclocymet, pyroquilon, phthalide, tricyclazole and a phenoxamide coded AC 382042, most preferred is AC 382042.

Preferred compounds of (D) are acibenzolar (BION), cyprodinil, dodine, ethirimol, famoxadone, fenpiclonil, fluazinam, mancozeb and metalaxyl.

Preferred azolopyrimidines of (E) are the compounds of formula IIA, (IIA)

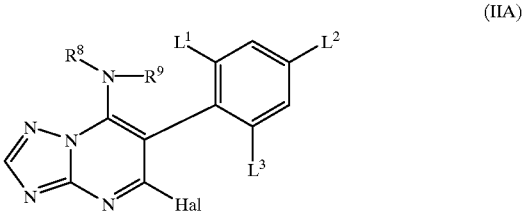

wherein
$R^8$ represents a $C_{1-8}$ alkyl, $C_{2-8}$ alkenyl, $C_{3-8}$ cycloalkyl or $C_{1-8}$ haloalkyl group, in particular, a straight-chained or branched $C_{3-6}$ alkyl, $C_{2-6}$ alkenyl, $C_{5-6}$ cycloalkyl or $C_{2-6}$ fluoroalkyl group, most preferably, an isopropyl, 2-butyl, cyclopentyl, methallyl, 2,2,2-trifluoroethyl or 1,1,1-trifluoroprop-2-yl group; and
$R^9$ represents a hydrogen atom, or a $C_{1-8}$ alkyl group; most preferably, a hydrogen atom or a methyl or ethyl group; or
$R^8$ and $R_9$ together form an optionally substituted alkylene group having 3 to 6 carbon atoms in the main chain, in which one $CH_2$ group may be replaced by O, S or NH, in particular, a piperid-1-yl group being optionally substituted by a $C_{1-6}$ alkyl group, most preferably, a 4-methylpiperid-1-yl group;

$L^1$, $L^2$ and $L^3$ each independently represent a hydrogen or halogen atom or a $C_{1-4}$ alkoxy group, at least one of which represents a halogen atom, in particular, wherein $L^1$ represents a fluorine atom, $L^2$ represents a hydrogen or fluorine atom or a methoxy group and $L^3$ represents a fluorine or chlorine atom; and Hal denotes a halogen atom, in particular, a chlorine atom.

Particularly preferred azolopyrimidines of formula II are 5-chloro-6-(2-chloro-6-fluorophenyl)-7-(cyclopropylamino)-[1,2,4]triazolo[1,5-a]pyrimidine (hereinafter coded AP-1), 5-chloro-6-(2-chloro-6-fluorophenyl)-7-(4-methylpiperid-1-yl)-[1,2,4]triazolo[1,5-a]pyrimidine (hereinafter coded AP-2), 5-chloro-6-(2-chloro-6-fluorophenyl)-7-(2,2,2-trifluoroethylamino)-[1,2,4]triazolo[1,5-a]pyrimidine (hereinafter coded AP-3) and 5-chloro-6-(2,4,6-trifluorophenyl)-7-[2-(1,1,1-trifluoro)propylamino]-[1,2,4]triazolo[1,5-a]pyrimidine coded (hereinafter AP-4), and, of these, most preferred is AP4.

Particularly preferred embodiments of this invention are compositions of three active ingredients which comprise one compound of formula I and two different compounds selected from (A), (B), (C), (D) and (E). Especially, preferred are compositions which include with the compound of formula I one strobilurine compound and one ergosterol biosynthesis inhibitor and most preferably, kresoxim-methyl and epoxiconazole, or kresoxim-methyl and fenpropimorph.

Other particularly preferred embodiments of the present invention are compositions comprising one compound of formula I and two different compounds of (D), in particular dimethomorph and mancozeb.

Highly preferred embodiments of this invention are co-formulations which comprise the following constituents:

at least one benzophenone of formula I, at least one compound selected from (A) through (E) as defined above;

a carrier;

optionally, an adjuvant selected from the group consisting of polyalkoxylated alcohols, triglycerides and amines; and optionally, a foam breaking agent.

Suitable polyalkoxylated alcohols for use in such formulations include, but are not limited to, polyalkoxylated alcohols based on alkoxy units having 2 carbon atoms, thus being a mixed ethoxylate, or 2 and 3 carbon atoms, thus being a mixed ethoxylate/propoxylate. In a preferred polyalkoxylated alcohol the alkoxylate chain may have at least 5 alkoxy moieties, suitably from 5 to 25 alkoxy moieties, preferably 5 to 20, in particular 5 to 15. The alcohol moiety of the alcohol alkoxylates is preferably derived from a C9–18 aliphatic alcohol. Preferred alcohols are typically about 50 % by weight straight-chained and about 50 % by weight branched alcohols. Particularly preferred are SynperonicG alcohol alkoxylates from Uniqema (formerly ICI Surfactants), in particular SynperonicG 91-6.

In accordance with the present invention, the compound of formula I and the compound selected from (A) through (E) as defined above are applied together, in synergistically effective amounts. These synergistic mixtures exhibit an extraordinary efficacy against a broad range of phytopathogenic fungi, in particular, against fungi from the classes ascomycetes, basidiomycetes, oomycetes and deuteromycetes. Therefore, they can be applied advantageously against a broad range of diseases in different crops. They may be applied as leaf, stem, root, into-water, seed dressing, nursery box or soil fungicides.

Thus, the synergistic mixture of the invention can be utilized to control phytopathogenic fungi of the genera: Achlya, Alternaria, Balansia, Bipolaris, Blumeria, Botrytis, Cercospora, Cochliobolus, Curvularia, Cylindrocladium, Drechslera, Entyloma, Erysiphe, Fusarium, Gaeumannomyces, Gerlachia, Gibberella, Guignardia, Leptosphaeria, Magnaporthe, Microsphaera, Molinia, Mucor, Mycosphaerella, Myrothecium, Nigrospora, Peronospora, Phaeosphaeria, Phoma, Phyllactinia, Phytophthora, Podosphaera, Pseudoperonospora, Pseudocercosporella, Puccinia, Pyrenophora, Pyricularia, Pythium, Rhizoctonia, Rhizopus, Rhynchosporium, Sarocladium, Sclerophthora, Sclerotium, Septoria, Sphaerotheca, Stagonospora, Tilletia, Uncinula, Ustilago, Ustilaginoidea, and Venturia, in particular the species *Blumeria graminis* f. sp. *tritici, Cercospora beticola, Septoria tritici, Erysiphe cichoracearum, Puccinia recondita* and *Pyrenophora teres*. The mixtures according to the invention are, in particular, applied for controlling the above phytopathogenic fungi on monocotylydoneous plants, such as barley and wheat, rice and turf grasses or fruit crops such as pomefruits, stonefruits and vines, as well as all kinds of vegetables and ornamentals.

The application rate of the compound of formula I according to this invention is usually in the range of 1 to 2000 grams of active ingredient (g a.i.) per hectare, with rates between 20–500 g a.i./ha often achieving satisfactory control. The optimal rate for a specific application will depend on the crop(s) under cultivation and the predominant species of infesting fungi, and readily may be determined by established biological tests known to those skilled in the art. In general, the preferred application rate of the compounds of formula I is in the range of 10 to 500 g a.i./ha, preferably 20–300 g a.i./ha.

The optimal rate of application for the compound of (A) through (E) will, however, depend on the crop(s) under cultivation and the level of infestation by the fungus, and can readily be determined by established biological tests.

The ratio (by weight) of the compound of formula I to the fungicidal active ingredient of the classes (A) through (E) as defined above is as a rule, from 100:1 to 1:100. The preferred ratio formula I: (A) through (E) may vary, for instance, from about 10:1 to about 1:10, particularly from about 5:1 to about 1:5, and most preferably from about 2:1 to 1:2.

In the three-ways-compositions according to the present invention, i.e., the compositions containing one compound of formula I and two different compounds from (A) through (E), the preferred relative ratios (by weight) are as follows:

compound of formula I: 200 to 1, preferably 20 to 1

1st compound of (A) to (E): 1 to 100, preferably 1 to 10

2nd compound of (A) to (E): 1 to 100, preferably 1 to 10.

The active compounds can be co-formulated together in a suitable ratio according to the present invention, together with usual carriers or diluents and/or additives known in the art.

Accordingly, the invention further provides a fungicidal composition which comprises a carrier and, as active ingredient, at least one compound of formula I as defined above and at least one fungicidally active compound selected from (A) through (E) as defined above.

A method of making such a composition is also provided which comprises bringing the compound of formula I and the fungicidally active compound selected from A) through (E) as defined above into association with at least one carrier. It is also envisaged that different isomers or mixtures of isomers of formula I and/or the fungicidally active ingredient selected from (A) through (E) may have different levels or spectra of activity, and thus compositions may comprise individual isomers or mixtures of isomers.

A composition according to the invention preferably contains from 0.1% to 99.9%, preferably, 0.2 to 80 % by weight (w/w) of active ingredients.

A carrier in a composition according to the invention is any material with which the active ingredient is formulated to facilitate application to the locus to be treated, which may be, for example, a plant, seed, foliage, soil, or into the water where the plant grows, or to the roots or to facilitate storage, transport or handling. A carrier may be a solid or a liquid, including material which is normally a gas but which has been compressed to form a liquid.

The compositions may be manufactured into conventional agrochemical formulations such as emulsion concentrates, solutions, oil in water emulsions, wettable powders, soluble powders, suspension concentrates, dusts, granules, water dispersible granules, tablets, micro-capsules, gels and other formulation types by well-established procedures. These procedures include intensive mixing and/or milling of the active ingredients with other substances, such as fillers, solvents, solid carriers, surface active compounds (surfactants), and optionally, solid and/or liquid auxilaries and/or adjuvants. The form of application such as spraying, atomizing, dispersing or pouring may be chosen, like the compositions, according to the desired objectives and the given circumstances.

Typical solvents include, but are not limited to, aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher N-alkylpyrrolidones, e.g. N-octylpyrrolidone or N-cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite or others. The physical properties of the formulations may be improved by addition of highly dispersed silica gel or polymers. Carriers for granules may be porous material, e.g. pumice, kaolin, sepiolite, bentonite; non-sorptive carriers may be calcite or sand or others. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may, for example, be formulated as wettable powders (WP), water dispersible granules (WG), dusts, granules, solutions (SL), emulsifiable concentrates (EC), emulsions, suspension concentrates (SC) and aerosols. Wettable powders usually contain 5 to 90% w/w of active ingredient and usually contain, in addition to solid inert carrier, 3 to 10% w/w of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizers, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example, compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the formulation or the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity, the compositions are preferably packaged in a concentrated form whereas the end user generally employs diluted compositions. The compositions may be diluted to a concentration down to 0.0001%, preferably down to 0.001%, in particular 0.002 to 0.05%, of one or more active ingredients. The doses usually are in the range from 0.01 to 10 kg a.i./ha.

In a preferred embodiment the active ingredients are added to the tank mix together each as a solo formulation.

Therefore, the present invention also relates to a kit for the preparation of a spray mixture consisting of two separate containers:

(i) a first container comprising at least one benzophenone of formula I in particular one or more compounds selected from BP-1, BP-2, BP-3 and BP-4, conventional carriers and optionally, adjuvants; and (ii) a second container comprising at least one active ingredient selected from (A) through (E).

In a preferred embodiment the kit will consist of two bottles with dispensing means which allow the easy and correct addition of the active ingredients to the tank mix.

The formulation SC-I+A–E comprising BP-4 and a fungicidally active ingredient selected from (A) through (E) as defined above can be used directly for preparing the tank mix according to the present invention.

The compositions of this invention can be applied to the plants or their environment simultaneous, or in succession, with other active substances. These other active substances can be either fertilizers, agents which donate trace elements, or other preparations which influence plant growth. However, they can also be other fungicides, selective herbicides, insecticides, bactericides, nematicides, algicides, molluscidides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

Examples of insecticidal compounds are alpha-cypermethrin, benfuracarb, BPMC, buprofezine, carbosulfan, cartap, chlorfenvinphos, chlorpyrifos-methyl, cycloprothrin, cypermethrin, esfenvalerate, ethofenprox, fenpropathrin, flucythrinate, flufenoxuron, hydramethyinon, imidacloprid, isoxathion, MEP, MPP, nitenpyram, PAP, permethrin, propaphos, pymetrozine, silafluofen, tebufenozide, teflubenzuron, temephos, terbufos, tetrachlorvinphos and triazamate.

Examples of biological control agents are: *Bacillus thuringiensis, Verticillium lecanii, Autographica californica* NPV, *Beauvaria bassiana, Ampelomyces quisqualis, Bacillis subtilis, Pseudomonas cholororaphis, Pseudomonas fluorescens, Steptomyces griseoviridis* and *Trichoderma harzianum*.

Examples of chemical agents that induce systemic acquired resistance in plants are those such as isonicotinic acid or derivatives thereof, 2,2-dichloro-3,3-dimethylcyclopropylcarboxylic acid.

The present invention is of wide applicability in the protection of crops, trees, residential and ornamental plants against fungal attack. Preferred crops are cereals, such as wheat and barley, rice as well as vines and apples. The duration of the protection is normally dependent on the individual compound selected, and also a variety of external factors, such as climate, whose impact is normally mitigated by the use of a suitable formulation.

The following examples further illustrate the present invention. It should be understood, however, that the invention is not limited solely to the particular examples given below.

EXAMPLES

Examples of formulations utilizable in the present invention are:

Suspension Concentrate of Formula I Compound (SC-I 1)

| active ingredient | BP-1 | 100.0 g |
|---|---|---|
| Dispersing agent | Morwet D425[1] | 25.0 g |
| Dispersing agent | Pluronic ® PE10500[2] | 5.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |

Suspension Concentrate of Formula I Compound (SC-I 2)

| active ingredient | BP-4 | 100.0 g |
|---|---|---|
| Dispersing agent | Soprophor ® FL[3] | 30.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |

Suspension Concentrate of (A) Through (E) Compound (SC-A–E)

| active ingredient | fungicide selected from classes (A) through (E) | 200.0 g |
|---|---|---|
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |

SC-I+A–E

| active ingredient | BP-4 | 60.0 g |
|---|---|---|
| active ingredient | fungicide selected from classes (A) through (E) | 120.0 g |
| Dispersing agent | Soprophor ® FL[3] | 25.0 g |
| Antifoaming agent | Rhodorsil ® 426R[3] | 1.5 g |
| Dispersing agent | Rhodopol ® 23[3] | 2.0 g |
| Antifreezing agent | Propylene glycol | 80.0 g |
| Biocidal agent | Proxel ® GXL[4] | 1.0 g |
| Water | | to 1000 ml |

DC-I 1

| active ingredient | BP-4 | 100.0 g |
|---|---|---|
| Wetting agent | Pluronic ® PE6400[2] | 50.0 g |
| Dispersing agent | Lutensol ® TO 12[2] | 50.0 g |
| Solvent | benzyl alcohol | to 1000 ml |

[1] Product commercially available from Witco
[2] Product commercially available from BASF AG, Germany
[3] Product commercially available from Rhône-Poulenc
[4] Product commercially available from Zeneca The formulation SC-A–E comprising a compound selected from (A) through (E) is in-tank mixed with any of the other formulations SC-I 1, SC-I 2, or DC-I which comprise a compound of formula I.

General Methods

The trials are carried out under greenhouse (Examples 1 to 18) or field conditions (Example 19) in residual or curative applications. The fungicides are applied in single treatments, or in a combination comprising a benzophenone of formula I and a compound selected from (A) through (E) as defined above. The compounds are applied in form of an aqueous spray mix obtained from a concentrated formulation or the technical material.

I. Cereals and Dicot Disease Control—Greenhouse Trials
1. Seed is planted in 6 cm diameter plastic pots and maintained in the greenhouse.
2. When the primary leaf is fully expanded (in the case of cereals) or several leaves are present (in the case of dicots), formulated test compounds are sprayed with a three nozzle overhead fungicide sprayer to near run-off. Alternatively, a single nozzle overhead track sprayer is used for application of the compounds to cereals at a rate of 200 liters/ha (l/ha). Plants are then allowed to air-dry.
3. Inoculation precedes treatment in the case of curative evaluations and follows treatment in case of residual evaluations. For inoculation of powdery mildew disease, plants are set up on greenhouse benches with bottom watering mats and inoculated by dusting them with conidia from infected plants. Between inoculation and treatment for curative evaluations and between treatment and inoculation for residual evaluations, plants are maintained in the greenhouse with bottom watering. For inoculation of non-powdery mildew diseases, an aqueous spore suspension of the pathogen is applied to the plant and the plants are kept 1–2 days in a moist infection chamber before being returned to the greenhouse where they are maintained by bottom watering.
4. Disease on the foliage as percent leaf area with disease symptoms/signs is evaluated about 7 days after inoculation. In the case of wheat, the tips and bases of the leaves are excluded from the evaluation.

$$\% \text{ disease control} = 100 - \frac{\% \text{ disease in treated plants}}{\% \text{ disease in untreated plants}} \times 100\%$$

Formulation, Reference Compounds and Controls
1. Technical compounds are formulated in a solvent/surfactant system consisting of 5% acetone and 0.05% Tween 20 in deionized water. Compounds are dissolved in acetone prior to addition of the water; the Tween 20 can be added through either the acetone or the water. Dilutions are made using the solvent/surfactant system. Formulated compounds are prepared using deionized water.
2. Two kinds of controls are included:
   Plants treated with the solvent/surfactant solution and inoculated (Solvent Blank).
   Untreated plants which are inoculated (Inoculated Control).
For the field study formulated benzophenones BP-1 through BP-4 and formulated compounds from (A) through (E) were used.

Evaluation of the Disease
Assessments of the diseases took place at the indicated day after the application of the compounds. Per cent infected leaf area infected was evaluated. The efficacy of the compounds/compounds mixtures to control the diseases was calculated by using the formula given above under item 4:

II. Apple Fruit Botrytis Rot Control
1. Apples (Malusxdomestica Borkh.) variety "Golden Delicious" are disinfected by washing them briefly in 70% ethanol. After drying the apples are marked with four short equal-distant lines indicating the positions to be wounded.
2. Corresponding with the marks, four holes are poked around the apple equator with a pipette tip. 10 µl of the treatment solution are pipetted into each hole.
3. Three hours after application, 10 µl of a conidial suspension of *Botrytis cinerea* are pipetted into each hole. For incubation, the treated/inoculated apples are stored for five days.
4. Disease occurs as rotten apple tissue surrounding the inoculated wounds. The diameter of the rotten zone around each wound is measured.

Formulation, Reference Compounds and Controls
1. Technical compounds are formulated in a solvent system consisting of 5% acetone and 0.05% Tween 20 in deionized water.
   Compounds are dissolved in acetone prior to dilution with water.
   Formulated compounds are prepared using deionized water.
2. Three kinds of controls are included:
   Apples treated with the solvent solution and inoculated (Solvent Blank).
   Untreated apples which are inoculated (Inoculated Control).
   Untreated apples which are not inoculated (Uninoculated Control).

Evaluation of the Disease
Assessments of the diseases took place at the indicated day after the application of the compounds. Per cent infected leaf area infected was evaluated. The efficacy of the compounds/compounds mixtures to control the diseases was calculated by using the formula:

$$\% \text{ disease control} = 100 - \frac{\text{mean of diameters on treated apples}}{\text{mean of diameters on untreated apples}} \times 100\%$$

Determination of Synergy
Synergy of a fungicide mixture was determined by comparing the actual (observed) fungicidal activity of the mixture to the expected fungicidal activity of the mixture as calculated using the COLBY formula given hereinabove. If the actual activity was greater than the expected activity the fungicidal mixture showed a synergistic effect.

III. Plant Disease Control—Field Trials
The compounds are applied according to good agricultural practice in form of an aqueous spray mix obtained from concentrated formulation or the technical material at a rate of 400 l/ha. The disease control is evaluated according to the formula given for the greenhouse tests.

A Greenhouse Tests

Example 1

Fungicidal Efficacy of the Mixture of BP-1+AP-1 (4 Day Curative) Against *Blumeria graminis* on Wheat The tank mix was obtained from technical materials of BP-1 and AP-1.

The observed and expected efficacies with different rates are given in Table I:

TABLE I

| dose rate (ppm) | | | |
|---|---|---|---|
| BP-1 | AP-1 | Observed Efficacy | Expected Efficacy |
| 125 | 0 | 42 | — |
| 25 | 0 | 1 | — |
| 0 | 125 | 0 | — |
| 0 | 25 | 0 | — |
| 125 | 125 | 56 | 42 |

TABLE I-continued

| dose rate (ppm) | | Observed Efficacy | Expected Efficacy |
|---|---|---|---|
| BP-1 | AP-1 | | |
| 125 | 25 | 54 | 42 |
| 25 | 125 | 21 | 1 |
| 25 | 25 | 4 | 1 |

Example 2

Fungicidal Efficacy of the Mixture of BP-1+AP-2 (4 Day Curative) Against *Blumeria graminis* on Wheat The tank mix was obtained from technical materials of BP-1 and AP-2.

The observed and expected efficacies with different rates are given in Table II:

TABLE II

| dose rate (ppm) | | Observed Efficacy | Expected Efficacy |
|---|---|---|---|
| BP-1 | AP-2 | | |
| 125 | 0 | 42 | — |
| 25 | 0 | 1 | — |
| 0 | 125 | 8 | — |
| 0 | 25 | 0 | — |
| 125 | 125 | 67 | 47 |
| 125 | 25 | 73 | 42 |
| 25 | 125 | 20 | 9 |
| 25 | 25 | 9 | 1 |

Example 3

Fungicidal Efficacy of the Mixture of BP-1+Triadimefon (4 Day Curative) Against *Blumeria graminis* on Wheat The tank mix was obtained from technical material of BP-1 and a wettable powder formulation containing 250 g/kg triadimefon. The observed and expected efficacies with different rates are given in Table III:

TABLE III

| dose rate (ppm) | | Observed Efficacy | Expected Efficacy |
|---|---|---|---|
| BP-1 | triadimefon | | |
| 125 | 0 | 42 | — |
| 25 | 0 | 1 | — |
| 0 | 125 | 30 | — |
| 0 | 25 | 12 | — |
| 125 | 125 | 85 | 59 |
| 125 | 25 | 56 | 49 |
| 25 | 125 | 41 | 31 |
| 25 | 25 | 6 | 13 |

Example 4

Fungicidal Efficacy of the Mixture of BP-5+Triforine (3 Day Protective) Against *Blumeria graminis* on Wheat The tank was obtained from technical material of BP-5 and an EC formulation containing 190 g/l triforine. The observed and expected efficacies with different rates are given in Table IV:

TABLE IV

| dose rate (ppm) | | Observed Efficacy | Expected Efficacy |
|---|---|---|---|
| BP-5 | triforine | | |
| 25 | 0 | 31 | — |
| 5 | 0 | 12 | — |
| 0 | 125 | 12 | — |
| 25 | 125 | 59 | 41 |
| 5 | 25 | 26 | 24 |

Example 5

Fungicidal Efficacy of the Mixture of BP-1+Triadimefon (3 Day Protective) Against *Blumeria graminis* on Wheat The tank mix was obtained from technical material of BP-1 and a wettable powder formulation containing 250 g/kg triadimefon. The observed and expected efficacies with different rates are given in Table V:

TABLE V

| dose rate (ppm) | | Observed Efficacy | Expected Efficacy |
|---|---|---|---|
| BP-1 | triadimefon | | |
| 5 | 0 | 78 | — |
| 1 | 0 | 44 | — |
| 0 | 25 | 24 | — |
| 5 | 25 | 90 | 83 |
| 1 | 25 | 78 | 57 |

Example 6

Fungicidal Efficacy of the Mixture of BP-4+Other Fungicides (4 Day Residual) Against *Erysiphe cichoracearum* on Cucumbers The tank mixes obtained from technical material (TC 100%) of BP-4 and different formulations of different active ingredients. The active ingredients, the type of formulations, the observed and expected efficacies with different rates are given in Table VI:

TABLE VI

| Compound | Formulation | dose rate (ppm) | Observed Efficacy | Expected Efficacy |
|---|---|---|---|---|
| BP-4 | TC 100% | 64 | 100 | |
| | | 16 | 51 | |
| | | 4 | 6 | |
| | | 1 | 1 | |
| Dithianon | WG 700 g/kg | 256 | 0 | |
| | | 64 | 0 | |
| | | 16 | 0 | |
| | | 4 | 0 | |
| Cyprodinil | TC 100% | 256 | 15 | |
| | | 64 | 0 | |
| | | 16 | 0 | |
| | | 4 | 0 | |
| Triforine | EC 190 g/l | 256 | 96 | |
| | | 64 | 79 | |
| | | 16 | 44 | |
| | | 4 | 1 | |
| Fenpropidin | EC 750 g/l | 256 | 69 | |
| | | 64 | 21 | |
| | | 16 | 6 | |
| | | 4 | 0 | |
| Mancozeb | WP 800 g/kg | 256 | 33 | |
| | | 64 | 1 | |
| | | 16 | 0 | |
| | | 4 | 0 | |

TABLE VI-continued

| Compound | Formulation | dose rate (ppm) | Observed Efficacy | Expected Efficacy |
|---|---|---|---|---|
| Quinoxyfen | TC 100% | 256 | 100 | |
| | | 64 | 100 | |
| | | 16 | 100 | |
| | | 4 | 90 | |
| Chlorothalonil | SC 500 g/l | 256 | 1 | |
| | | 64 | 0 | |
| | | 16 | 0 | |
| | | 4 | 0 | |
| Ethirimol | SC 280 g/l | 256 | 100 | |
| | | 64 | 94 | |
| | | 16 | 83 | |
| | | 4 | 50 | |
| Dimethomorph | TC 100% | 256 | 18 | |
| | | 64 | 0 | |
| | | 16 | 0 | |
| | | 4 | 0 | |
| BION | WG 500 g/kg | 256 | 0 | |
| | | 64 | 0 | |
| | | 16 | 0 | |
| | | 4 | 0 | |
| Azoxystrobin | TC 100% | 256 | 100 | |
| | | 64 | 100 | |
| | | 16 | 96 | |
| | | 4 | 78 | |
| BP-4 + Dithianon | Tankmix | 64 + 256 | 100 | 100 |
| | | 16 + 64 | 73 | 51 |
| | | 4 + 16 | 31 | 6 |
| | | 1 + 4 | 29 | 1 |
| BP-4 + Cyprodinil | Tankmix | 64 + 256 | 92 | 100 |
| | | 16 + 64 | 59 | 51 |
| | | 4 + 16 | 51 | 6 |
| | | 1 + 4 | 32 | 1 |
| BP-4 + Triforine | Tankmix | 64 + 256 | 100 | 100 |
| | | 16 + 64 | 99 | 90 |
| | | 4 + 16 | 65 | 47 |
| | | 1 + 4 | 31 | 3 |
| BP-4 + Fenpropidin | Tankmix | 64 + 256 | 100 | 100 |
| | | 16 + 64 | 96 | 61 |
| | | 4 + 16 | 60 | 12 |
| | | 1 + 4 | 56 | 1 |
| BP-4 + Mancozeb | Tankmix | 64 + 256 | 100 | 100 |
| | | 16 + 64 | 99 | 52 |
| | | 4 + 16 | 54 | 6 |
| | | 1 + 4 | 38 | 1 |
| BP-4 + Quinoxyfen | Tankmix | 64 + 256 | 100 | 100 |
| | | 16 + 64 | 100 | 100 |
| | | 4 + 16 | 100 | 100 |
| | | 1 + 4 | 100 | 91 |
| BP-4 + Chlorothalonil | Tankmix | 64 + 256 | 100 | 100 |
| | | 16 + 64 | 99 | 51 |
| | | 4 + 16 | 22 | 6 |
| | | 1 + 4 | 14 | 1 |
| BP-4 + Ethirimol | Tankmix | 64 + 256 | 100 | 100 |
| | | 16 + 64 | 100 | 97 |
| | | 4 + 16 | 85 | 84 |
| | | 1 + 4 | 53 | 51 |
| BP-4 + Dimethomorph | Tankmix | 64 + 256 | 100 | 100 |
| | | 16 + 64 | 99 | 51 |
| | | 4 + 16 | 37 | 6 |
| | | 1 + 4 | 10 | 1 |
| BP-4 + BION | Tankmix | 64 + 256 | 100 | 100 |
| | | 16 + 64 | 53 | 51 |
| | | 4 + 16 | 12 | 6 |
| | | 1 + 4 | 1 | 1 |
| BP-4 + Azoxystrobin | Tankmix | 64 + 256 | 100 | 100 |
| | | 16 + 64 | 100 | 100 |
| | | 4 + 16 | 99 | 96 |
| | | 1 + 4 | 92 | 78 |

Example 7
Fungicidal Efficacy of the Mixture of BP-4+Other Fungicides (4 Day Residual) Against *Puccinia recondita* on Wheat The tank mixes were obtained from technical material of BP-4 and different formulations of different active ingredients. The active ingredients, the type of formulations, the observed and expected efficacies with different rates are given in Table VII:

TABLE VII

| Compound | Formulation | dose rate (ppm) | Observed Efficacy | Expected Efficacy |
|---|---|---|---|---|
| BP-4 | TC 100% | 256 | 13 | |
| | | 64 | 0 | |
| | | 16 | 0 | |
| | | 4 | 0 | |
| Dithianon | WG 700 g/kg | 256 | 95 | |
| | | 64 | 84 | |
| | | 16 | 16 | |
| | | 4 | 4 | |
| Cyprodinil | TC 100% | 256 | 0 | |
| | | 64 | 0 | |
| | | 16 | 0 | |
| | | 4 | 0 | |
| Triforine | EC 190 g/l | 256 | 100 | |
| | | 64 | 90 | |
| | | 16 | 7 | |
| | | 4 | 0 | |
| Fenpropidin | EC 750 g/l | 256 | 97 | |
| | | 64 | 8 | |
| | | 16 | 0 | |
| | | 4 | 0 | |
| Mancozeb | WP 800 g/kg | 256 | 91 | |
| | | 64 | 28 | |
| | | 16 | 0 | |
| | | 4 | 0 | |
| Quinoxyfen | TC 100% | 256 | 0 | |
| | | 64 | 0 | |
| | | 16 | 0 | |
| | | 4 | 0 | |
| Chlorothalonil | SC 500 g/l | 256 | 31 | |
| | | 64 | 0 | |
| | | 16 | 0 | |
| | | 4 | 0 | |
| Ethirimol | SC 280 g/l | 256 | 0 | |
| | | 64 | 0 | |
| | | 16 | 0 | |
| Dimethomorph | TC 100% | 256 | 0 | |
| | | 64 | 0 | |
| | | 16 | 0 | |
| BION | WG 500 g/kg | 256 | 0 | |
| | | 64 | 0 | |
| | | 16 | 0 | |
| | | 4 | 0 | |
| BP-4 + Dithianon | Tankmix | 256 + 256 | 100 | 95 |
| | | 64 + 64 | 100 | 84 |
| | | 16 + 16 | 100 | 16 |
| | | 4 + 4 | 100 | 4 |
| BP-4 + Cyprodinil | Tankmix | 256 + 256 | 100 | 13 |
| | | 64 + 64 | 100 | 0 |
| | | 16 + 16 | 100 | 0 |
| | | 4 + 4 | 100 | 0 |
| BP-4 + Triforine | Tankmix | 256 + 256 | 100 | 100 |
| | | 64 + 64 | 100 | 90 |
| | | 16 + 16 | 100 | 7 |
| | | 4 + 4 | 100 | 0 |
| BP-4 + Fenpropidin | Tankmix | 256 + 256 | 100 | 97 |
| | | 64 + 64 | 96 | 8 |
| | | 16 + 16 | 93 | 0 |
| | | 4 + 4 | 91 | 0 |
| BP-4 + Mancozeb | Tankmix | 256 + 256 | 100 | 92 |
| | | 64 + 64 | 97 | 28 |
| | | 16 + 16 | 94 | 0 |
| | | 4 + 4 | 92 | 0 |
| BP-4 + Quinoxyfen | Tankmix | 256 + 256 | 89 | 13 |
| | | 64 + 64 | 96 | 0 |
| | | 16 + 16 | 95 | 0 |
| | | 4 + 4 | 93 | 0 |
| BP-4 + Chlorothalonil | Tankmix | 256 + 256 | 100 | 40 |
| | | 64 + 64 | 36 | 0 |
| | | 16 + 16 | 40 | 0 |
| | | 4 + 4 | 9 | 0 |
| BP-4 + | Tankmix | 256 + 256 | 96 | 13 |

TABLE VII-continued

| Compound | Formulation | dose rate (ppm) | Observed Efficacy | Expected Efficacy |
|---|---|---|---|---|
| Ethirimol | | 64 + 64 | 96 | 0 |
| | | 16 + 16 | 64 | 0 |
| BP-4 + Dimethomorph | Tankmix | 256 + 256 | 54 | 13 |
| | | 64 + 64 | 28 | 0 |
| | | 16 + 16 | 6 | 0 |
| BP-4 + BION | Tankmix | 256 + 256 | 75 | 13 |
| | | 64 + 64 | 78 | 0 |
| | | 16 + 16 | 64 | 0 |
| | | 4 + 4 | 59 | 0 |

Example 8

Fungicidal Efficacy of the Mixture of BP-4+Other Fungicides (4 Day Residual) Against *Leptosphaeria nodorum* on Wheat The tank mixes were obtained from technical material of BP-4 and different formulations of different active ingredients. The active ingredients, the type of formulations, the observed and expected efficacies with different rates are given in Table VIII:

TABLE VIII

| Compound | Formulation | dose rate (ppm) | Observed Efficacy | Expected Efficacy |
|---|---|---|---|---|
| BP-4 | TC 100% | 256 | 34 | |
| | | 64 | 14 | |
| | | 16 | 0 | |
| | | 4 | 0 | |
| Dithianon | WG 700 g/kg | 256 | 74 | |
| | | 64 | 37 | |
| | | 16 | 1 | |
| | | 4 | 0 | |
| Cyprodinil | TC 100% | 256 | 93 | |
| | | 64 | 88 | |
| | | 16 | 75 | |
| | | 4 | 0 | |
| Triforine | EC 190 g/l | 256 | 85 | |
| | | 64 | 51 | |
| | | 16 | 31 | |
| | | 4 | 4 | |
| | | 1 | 0 | |
| Fenpropidin | EC 750 g/l | 256 | 21 | |
| | | 64 | 0 | |
| Mancozeb | WP 800 g/kg | 256 | 69 | |
| | | 64 | 47 | |
| | | 16 | 21 | |
| | | 4 | 0 | |
| Quinoxyfen | TC 100% | 256 | 18 | |
| | | 64 | 0 | |
| | | 16 | 1 | |
| Dimethomorph | TC 100% | 256 | 14 | |
| | | 64 | 11 | |
| | | 16 | 6 | |
| | | 4 | 1 | |
| Azoxystrobin | TC 100% | 256 | 100 | |
| | | 64 | 100 | |
| | | 16 | 97 | |
| | | 4 | 84 | |
| BP-4 + Dithianon | Tankmix | 256 + 256 | 90 | 83 |
| | | 64 + 64 | 65 | 46 |
| | | 16 + 16 | 27 | 1 |
| | | 4 + 4 | 4 | 0 |
| BP-4 + Cyprodinil | Tankmix | 256 + 256 | 97 | 96 |
| | | 64 + 64 | 92 | 90 |
| | | 16 + 16 | 80 | 75 |
| | | 4 + 4 | 57 | 0 |
| BP-4 + Triforine | Tankmix | 256 + 256 | 97 | 90 |
| | | 64 + 64 | 84 | 58 |

TABLE VIII-continued

| Compound | Formulation | dose rate (ppm) | Observed Efficacy | Expected Efficacy |
|---|---|---|---|---|
| | | 16 + 16 | 47 | 31 |
| | | 4 + 4 | 32 | 4 |
| BP-4 + Fenpropidin | Tankmix | 256 + 256 | 42 | 48 |
| | | 64 + 64 | 21 | 14 |
| BP-4 + Mancozeb | Tankmix | 256 + 256 | 87 | 79 |
| | | 64 + 64 | 65 | 55 |
| | | 16 + 16 | 32 | 21 |
| | | 4 + 4 | 8 | 0 |
| BP-4 + Quinoxyfen | Tankmix | 256 + 256 | 62 | 46 |
| | | 64 + 64 | 34 | 14 |
| | | 16 + 16 | 8 | 1 |
| BP-4 + CL 336 370 Dimethomorph | Tankmix | 256 + 256 | 84 | 43 |
| | | 64 + 64 | 65 | 24 |
| | | 16 + 16 | 31 | 6 |
| | | 4 + 4 | 14 | 1 |
| BP-4 + Azoxystrobin | Tankmix | 256 + 256 | 100 | 100 |
| | | 64 + 64 | 100 | 100 |
| | | 16 + 16 | 98 | 97 |
| | | 4 + 4 | 95 | 84 |

Example 9

Fungicidal Efficacy of the Mixture of BP-4+Other Fungicides (4 Day Residual) Against *Puccinia recondita* on Wheat The tank mixes were obtained from technical material of BP-4 and different formulations of different active ingredients. The active ingredients, the type of formulations, the observed and expected efficacies with different rates are given in Table IX:

TABLE IX

| Compound | Formulation | dose rate (ppm) | Observed Efficacy | Expected Efficacy |
|---|---|---|---|---|
| BP-4 | TC 100% | 256 | 38 | |
| | | 64 | 16 | |
| | | 16 | 4 | |
| | | 4 | 6 | |
| Captan | WP 500 g/kg | 256 | 89 | |
| | | 64 | 55 | |
| | | 16 | 11 | |
| | | 4 | 4 | |
| Fluazinam | SC 500 g/l | 256 | 80 | |
| | | 64 | 22 | |
| | | 16 | 6 | |
| | | 4 | 0 | |
| Metalaxyl | TC 100% | 256 | 12 | |
| | | 64 | 0 | |
| Fenpiclonil | TC 100% | 256 | 58 | |
| | | 64 | 18 | |
| | | 16 | 0 | |
| | | 4 | 1 | |
| Famoxadone | TC 100% | 64 | 92 | |
| | | 16 | 80 | |
| | | 4 | 45 | |
| BP-4 + Captan | Tankmix | 256 + 256 | 95 | 93 |
| | | 64 + 64 | 65 | 62 |
| | | 16 + 16 | 30 | 15 |
| BP-4 + Fluazinam | Tankmix | 256 + 256 | 97 | 88 |
| | | 64 + 64 | 53 | 35 |
| | | 16 + 16 | 20 | 10 |
| BP-4 + Metalaxyl | Tankmix | 256 + 256 | 61 | 46 |
| | | 64 + 64 | 19 | 16 |
| BP-4 + | Tankmix | 256 + 256 | 81 | 74 |

TABLE IX-continued

| Compound | Formulation | dose rate (ppm) | Observed Efficacy | Expected Efficacy |
|---|---|---|---|---|
| Fenpiclonil | | 64 + 64 | 54 | 31 |
| | | 16 + 16 | 12 | 4 |
| | | 4 + 4 | 7 | 7 |
| BP-4 + Famoxadone | Tankmix | 64 + 64 | 93 | 93 |
| | | 16 + 16 | 83 | 81 |
| | | 4 + 4 | 60 | 48 |

Example 10

Fungicidal Efficacy of the Mixture of BP-4+Other Fungicides (4 Day Residual) Against *Leptosphaeria nodorum* on Wheat The tank mixes were obtained from technical material of BP-4 and different formulation of different ingredients. The active ingredients, the type of formulations, the observed and expected efficacies with different rates are given in Table X:

TABLE X

| Compound | Formulation | dose rate (ppm) | Observed Efficacy | Expected Efficacy |
|---|---|---|---|---|
| BP-4 | TC 100% | 256 | 44 | |
| | | 64 | 18 | |
| | | 16 | 10 | |
| | | 4 | 0 | |
| Dodine | WP 650 g/kg | 256 | 59 | |
| | | 64 | 24 | |
| | | 16 | 6 | |
| | | 4 | 0 | |
| Captan | WP 500 g/kg | 256 | 90 | |
| | | 64 | 84 | |
| Fluazinam | SC 500 g/l | 256 | 91 | |
| | | 64 | 81 | |
| Famoxadone | TC 100% | 256 | 97 | |
| | | 64 | 80 | |
| | | 16 | 69 | |
| | | 4 | 66 | |
| BP-4 + Dodine | Tankmix | 256 + 256 | 75 | 77 |
| | | 64 + 64 | 57 | 38 |
| | | 16 + 16 | 29 | 15 |
| | | 4 + 4 | 10 | 0 |
| BP-4 + Captan | Tankmix | 256 + 256 | 96 | 94 |
| | | 64 + 64 | 93 | 87 |
| BP-4 + Fluazinam | Tankmix | 256 + 256 | 95 | 95 |
| | | 64 + 64 | 91 | 84 |
| BP-4 + Famoxadone | Tankmix | 256 + 256 | 94 | 98 |
| | | 64 + 64 | 89 | 84 |
| | | 16 + 16 | 86 | 72 |
| | | 4 + 4 | 67 | 66 |

Example 11

Fungicidal Efficacy of the Mixture of BP-4+Other Fungicidal (4 Day Residual) Against *Erysiphe cichoracearum* on Cucumbers The tank mixes were obtained from technical material of BP-4 and different formulations of different active ingredients. The active ingredients, the type of formulations, observed and expected efficacies with different rates are given in Table XI:

TABLE XI

| Compound | Formulation | dose rate (ppm) | Observed Efficacy | Expected Efficacy |
|---|---|---|---|---|
| BP-4 | TC 100% | 50 | 96 | |
| | | 10 | 55 | |
| | | 2 | 2 | |
| | | 0.4 | 0 | |
| Sulfur organic | TC 100% | 50 | 0 | |
| | | 10 | 7 | |
| | | 2 | 0 | |
| | | 0.4 | 0 | |
| Propiconazole | EC 250 g/l | 50 | 96 | |
| | | 10 | 76 | |
| | | 2 | 19 | |
| | | 0.4 | 0 | |
| Epoxiconazole | SC 125 g/l | 50 | 77 | |
| | | 10 | 68 | |
| | | 2 | 46 | |
| | | 0.4 | 0 | |
| Tebuconazole | EC 250 g/l | 50 | 95 | |
| | | 10 | 79 | |
| | | 2 | 45 | |
| | | 0.4 | 10 | |
| Metconazole | SL 60 g/l | 50 | 99 | |
| | | 10 | 75 | |
| | | 0.4 | 2 | |
| Myclobutanil | WP 60 g/kg | 50 | 96 | |
| | | 10 | 73 | |
| | | 2 | 52 | |
| | | 0.4 | 36 | |
| Kresoxim-methyl | WG 500 g/kg | 50 | 100 | |
| | | 10 | 88 | |
| | | 2 | 14 | |
| | | 0.4 | 2 | |
| AC 382042 | TC 100% | 50 | 25 | |
| | | 10 | 14 | |
| | | 2 | 3 | |
| | | 0.4 | 7 | |
| BRIO Epoxiconazole/ Fenpropimorph (150 g/l)/ (300 g/l) | SE 450 g/l | 50 | 96 | |
| | | 10 | 48 | |
| ACROBAT MZ Dimethomorph/ Mancozeb (90 g/kg)/ (600 g/kg) | WP 690 g/kg | 50 | 57 | |
| | | 10 | 30 | |
| | | 2 | 0 | |
| | | 0.4 | 0 | |
| JUWEL Kresoxim-methyl/ Epoxiconazole. (125 g/l)/ (125 g/l) | SC 250 g/l | 50 | 100 | |
| | | 10 | 98 | |
| | | 2 | 71 | |
| | | 0.4 | 37 | |
| BP-4 Sulfur inorganic | Tankmix | 50 + 50 | 92 | 96 |
| | | 10 + 10 | 70 | 58 |
| | | 2 + 2 | 10 | 2 |
| | | 0.4+0.4 | 9 | 0 |
| BP-4 Propiconazole | Tankmix | 50 + 50 | 100 | 100 |
| | | 10 + 10 | 100 | 89 |
| | | 2 + 2 | 61 | 21 |
| | | 0.4+0.4 | 28 | 0 |
| BP-4 Epoxiconazole | Tankmix | 50 + 50 | 100 | 99 |
| | | 10 + 10 | 98 | 86 |
| | | 2 + 2 | 71 | 47 |
| | | 0.4+0.4 | 41 | 0 |
| BP-4 Tebuconazole | Tankmix | 50 + 50 | 100 | 100 |
| | | 10 + 10 | 98 | 91 |
| | | 2 + 2 | 48 | 45 |
| | | 0.4+0.4 | 28 | 10 |
| BP-4 Metconazole | Tankmix | 50 + 50 | 100 | 100 |
| | | 10 + 10 | 97 | 89 |
| | | 0.4+0.4 | 5 | 2 |
| BP-4 Myclobutanil | Tankmix | 50 + 50 | 100 | 100 |
| | | 10 + 10 | 99 | 88 |
| | | 2 + 2 | 75 | 52 |
| | | 0.4+0.4 | 55 | 36 |

TABLE XI-continued

| Compound | Formulation | dose rate (ppm) | Observed Efficacy | Expected Efficacy |
|---|---|---|---|---|
| BP-4 | Tankmix | 50 + 50 | 100 | 100 |
| Kresoxim-methyl | | 10 + 10 | 100 | 95 |
| | | 2 + 2 | 37 | 15 |
| | | 0.4+0.4 | 2 | 2 |
| BP-4 | Tankmix | 50 + 50 | 100 | 97 |
| AC 382042 | | 10 + 10 | 87 | 62 |
| | | 2 + 2 | 28 | 5 |
| | | 0.4+0.4 | 25 | 7 |
| BP-4 | Tankmix | 50 + 50 | 100 | 100 |
| BRIO | | 10 + 10 | 85 | 77 |
| BP-4 | Tankmix | 50 + 50 | 100 | 98 |
| ACROBAT MZ | | 10 + 10 | 89 | 69 |
| | | 2 + 2 | 45 | 2 |
| | | 0.4+0.4 | 7 | 0 |
| BP-4 | Tankmix | 50 + 50 | 100 | 100 |
| JUWEL | | 10 + 10 | 98 | 99 |
| | | 2 + 2 | 84 | 72 |
| | | 0.4 + 0.4 | 50 | 37 |

Example 12

Fungicidal Efficacy of the Mixture of BP-4+Myclobutanil (4 Day Residual) Against *Puccinia recondita* on Wheat The tank mixes were obtained from technical material of BP4 and Myclobutanil. The type of formulation, the observed and expected efficacies with different rates are given in Table XII:

TABLE XII

| Compound | Formulation | dose rate (ppm) | Observed Efficacy | Expected Efficacy |
|---|---|---|---|---|
| BP-4 | TC 100% | 50 | 31 | |
| | | 10 | 10 | |
| | | 2 | 7 | |
| | | 0.4 | 2 | |
| Myclobutanil | WP 60 g/kg | 50 | 99 | |
| | | 10 | 72 | |
| | | 2 | 52 | |
| | | 0.4 | 13 | |
| BP-4 Myclobutanil | Tankmix | 50 + 50 | 99 | 99 |
| | | 10 + 10 | 86 | 75 |
| | | 2 + 2 | 65 | 55 |
| | | 0.4 + 0.4 | 48 | 14 |

Example 13

Fungicidal Efficacy of the Mixture of BP-4+Other Fungicides (4 Day Residual) Against *Pyrenophora teres* on Barley The tank mixes were obtained from technical material of BP-4 and different formulations of different active ingredients. The active ingredients, the type of formulations, the observed and expected efficacies with different rates are given in Table XIII:

TABLE XIII

| Compound | Formulation | dose rate (ppm) | Observed Efficacy | Expected Efficacy |
|---|---|---|---|---|
| BP-4 | TC 100% | 50 | 58 | |
| | | 10 | 34 | |
| | | 2 | 0 | |
| | | 0.4 | 0 | |
| Sulfur | TC 100% | 10 | 0 | |

TABLE XIII-continued

| Compound | Formulation | dose rate (ppm) | Observed Efficacy | Expected Efficacy |
|---|---|---|---|---|
| inorganic | | 2 | 0 | |
| Copper oxychloride | WP 450 g/kg | 50 | 14 | |
| | | 10 | 14 | |
| | | 2 | 0 | |
| | | 0.4 | 0 | |
| Propiconazole | EC 250 g/l | 50 | 74 | |
| | | 10 | 38 | |
| | | 2 | 0 | |
| | | 0.4 | 0 | |
| Metconazole | SL 60 g/l | 10 | 47 | |
| | | 0.4 | 0 | |
| Myclobutanil | WP 60 g/kg | 50 | 82 | |
| | | 10 | 40 | |
| | | 2 | 21 | |
| | | 0.4 | 0 | |
| Kresoxim-methyl | WG 500 g/kg | 2 | 21 | |
| | | 0.4 | 0 | |
| ACROBAT MZ | WP 690 g/kg | 50 | 47 | |
| Dimethomorph/Mancozeb | | 10 | 23 | |
| | | 2 | 12 | |
| | | 0.4 | 0 | |
| JUWEL Kresoxim-methyl/Epoxiconazole | SC 250 g/l | 50 | 89 | |
| | | 10 | 62 | |
| | | 2 | 45 | |
| | | 0.4 | 5 | |
| BP-4 Sulfur inorganic | Tankmix | 10 + 10 | 49 | 34 |
| | | 2 + 2 | 0 | 0 |
| BP-4 Copper oxychloride | Tankmix | 50 + 50 | 78 | 64 |
| | | 10 + 10 | 54 | 43 |
| | | 2 + 2 | 38 | 0 |
| | | 0.4 + 0.4 | 0 | 0 |
| BP-4 Propiconazole | Tankmix | 50 + 50 | 89 | 89 |
| | | 10 + 10 | 78 | 59 |
| | | 2 + 2 | 32 | 0 |
| | | 0.4 + 0.4 | 0 | 0 |
| BP-4 Tebuconazole | Tankmix | 50 + 50 | 89 | 86 |
| | | 2 + 2 | 14 | 5 |
| | | 0.4 + 0.4 | 0 | 0 |
| BP-4 Metconazole | Tankmix | 10 + 10 | 69 | 65 |
| | | 2 + 2 | 25 | 32 |
| | | 0.4 + 0.4 | 18 | 0 |
| BP-4 Myclobutanil | Tankmix | 50 + 50 | 91 | 93 |
| | | 10 + 10 | 67 | 61 |
| | | 2 + 2 | 40 | 21 |
| | | 0.4 + 0.4 | 7 | 0 |
| BP-4 Kresoxim-methyl | Tankmix | 2 + 2 | 67 | 21 |
| | | 0.4 + 0.4 | 36 | 0 |
| BP-4 ACROBAT MZ | Tankmix | 50 + 50 | 85 | 78 |
| | | 10 + 10 | 60 | 49 |
| | | 2 + 2 | 29 | 12 |
| | | 0.4 + 0.4 | 0 | 0 |
| BP-4 JUWEL | Tankmix | 50 + 50 | 100 | 95 |
| | | 10 + 10 | 78 | 75 |
| | | 2 + 2 | 49 | 45 |
| | | 0.4 + 0.4 | 40 | 5 |

Example 14

Fungicidal Efficacy of the Mixture of BP-4+Other Fungicides (4 Day Residual) Against *Erysiphe cichoracearum* on Cucumbers The tank mixes were obtained from technical material of BP-4 and different formulations of different active ingredients. The active ingredients, the type of formulations, the observed and expected efficacies with different rates are given in Table XIV:

TABLE XIV

| Compound | Formulation | dose rate (ppm) | Observed Efficacy | Expected Efficacy |
|---|---|---|---|---|
| BP-4 | TC 100% | 50 | 97 | |
| | | 10 | 13 | |
| | | 2 | 0 | |
| | | 0.4 | 0 | |
| Cyproconazole | SL 100 g/l | 10 | 68 | |
| | | 0.4 | 19 | |
| Dinocap | WP 190 g/kg | 10 | 0 | |
| | | 2 | 0 | |
| | | 0.4 | 0 | |
| Fenarimol | SC 125 g/l | 50 | 67 | |
| | | 10 | 42 | |
| | | 2 | 34 | |
| | | 0.4 | 5 | |
| Fenpropimorph | EC 750 g/l | 10 | 7 | |
| | | 2 | 0 | |
| | | 0.4 | 0 | |
| Flusilazole | WP 200 g/kg | 50 | 38 | |
| | | 10 | 19 | |
| | | 2 | 0 | |
| | | 0.4 | 0 | |
| Penconazole | EC 100 g/l | 50 | 67 | |
| | | 10 | 37 | |
| | | 2 | 35 | |
| | | 0.4 | 6 | |
| Prochloraz | EC 400 g/l | 50 | 18 | |
| | | 10 | 1 | |
| | | 2 | 0 | |
| | | 0.4 | 0 | |
| Pyrifenox | WP 500 g/kg | 50 | 20 | |
| | | 10 | 1 | |
| | | 2 | 0 | |
| | | 0.4 | 0 | |
| Triadimefon | WP 250 g/kg | 50 | 47 | |
| | | 10 | 23 | |
| | | 2 | 6 | |
| | | 0.4 | 0 | |
| Triadimenol | EC 250 g/l | 50 | 68 | |
| | | 10 | 45 | |
| | | 2 | 21 | |
| | | 0.4 | 1 | |
| Spiroxamine | EC 500 g/l | 10 | 2 | |
| | | 2 | 0 | |
| | | 0.4 | 0 | |
| BP-4 Cyproconazole | Tankmix | 10 + 10 | 84 | 72 |
| | | 0.4 + 0.4 | 23 | 19 |
| BP-4 Dinocap | Tankmix | 50 + 50 | 96 | 98 |
| | | 10 + 10 | 30 | 13 |
| | | 2 + 2 | 2 | 0 |
| | | 0.4 + 0.4 | 2 | 0 |
| BP-4 Fenarimol | Tankmix | 50 + 50 | 100 | 99 |
| | | 10 + 10 | 92 | 49 |
| | | 2 + 2 | 49 | 34 |
| | | 0.4 + 0.4 | 19 | 5 |
| BP-4 Fenpropimorph | Tankmix | 10 + 10 | 43 | 19 |
| | | 2 + 2 | 6 | 0 |
| | | 0.4 + 0.4 | 2 | 0 |
| BP-4 Flusilazole | Tankmix | 50 + 50 | 100 | 98 |
| | | 10 + 10 | 57 | 29 |
| | | 2 + 2 | 14 | 0 |
| | | 0.4 + 0.4 | 1 | 0 |
| BP-4 Penconazole | Tankmix | 50 + 50 | 100 | 99 |
| | | 10 + 10 | 96 | 45 |
| | | 2 + 2 | 66 | 35 |
| | | 0.4 + 0.4 | 23 | 6 |
| BP-4 Prochloraz | Tankmix | 50 + 50 | 100 | 98 |
| | | 10 + 10 | 71 | 13 |
| | | 2 + 2 | 11 | 0 |
| | | 0.4 + 0.4 | 7 | 0 |
| BP-4 Pyrifenox | Tankmix | 50 + 50 | 100 | 98 |
| | | 10 + 10 | 56 | 13 |
| | | 2 + 2 | 7 | 0 |
| | | 0.4 + 0.4 | 4 | 0 |
| BP-4 Triadimefon | Tankmix | 50 + 50 | 99 | 99 |
| | | 10 + 10 | 39 | 32 |
| | | 2 + 2 | 15 | 6 |
| | | 0.4 + 0.4 | 2 | 0 |
| BP-4 Triadimenol | Tankmix | 50 + 50 | 100 | 99 |
| | | 10 + 10 | 78 | 52 |
| | | 2 + 2 | 30 | 21 |
| | | 0.4 + 0.4 | 9 | 1 |
| BP-4 Spiroxamine | Tankmix | 10 + 10 | 37 | 15 |
| | | 2 + 2 | 10 | 0 |
| | | 0.4 + 0.4 | 2 | 0 |

Example 15

Fungicidal Efficacy of the Mixture of BP-4+Other Fungicides (4 Day Residual) Against *Puccinia recondita* on Wheat The tank mixes were obtained from technical material of BP-4 and different formulations of different active ingredients. The active ingredients, the type of formulations, the observed and expected efficacies with different rates are given in Table XV:

TABLE XV

| Compound | Formulation | dose rate (ppm) | Observed Efficacy | Expected Efficacy |
|---|---|---|---|---|
| BP-4 | TC 100% | 50 | 12 | |
| | | 10 | 6 | |
| | | 2 | 0 | |
| | | 0.4 | 0 | |
| Cyproconazole | SL 100 g/l | 2 | 99 | |
| | | 0.4 | 88 | |
| Dinocap | WP 190 g/kg | 50 | 54 | |
| | | 10 | 23 | |
| | | 2 | 13 | |
| | | 0.4 | 4 | |
| Fenarimol | SC 125 g/l | 50 | 90 | |
| | | 10 | 23 | |
| | | 2 | 9 | |
| | | 0.4 | 0 | |
| Fenpropimorph | EC 750 g/l | 50 | 60 | |
| | | 2 | 15 | |
| | | 0.4 | 2 | |
| Flusilazole | WP 200 g/kg | 50 | 100 | |
| | | 2 | 28 | |
| | | 0.4 | 5 | |
| Penconazole | EC 100 g/l | 50 | 26 | |
| | | 10 | 10 | |
| | | 2 | 3 | |
| | | 0.4 | 0 | |
| Prochloraz | EC 400 g/l | 50 | 14 | |
| | | 16 | 1 | |
| | | 2 | 0 | |
| | | 0.4 | 0 | |
| Pyrifenox | WP 500 g/kg | 50 | 6 | |
| | | 10 | 1 | |
| | | 2 | 0 | |
| | | 0.4 | 0 | |
| Triadimenol | EC 250 g/l | 50 | 98 | |
| | | 10 | 69 | |
| | | 2 | 21 | |
| | | 0.4 | 1 | |
| Spiroxamine | EC 500 g/l | 50 | 17 | |
| | | 10 | 4 | |
| | | 2 | 0 | |
| BP-4 Cyproconazole | Tankmix | 2 + 2 | 100 | 99 |
| | | 0.4 + 0.4 | 92 | 88 |
| BP-4 Dinocap | Tankmix | 50 + 50 | 61 | 60 |
| | | 10 + 10 | 38 | 28 |
| | | 2 + 2 | 26 | 13 |
| | | 0.4 + 0.4 | 10 | 4 |
| BP-4 | Tankmix | 50 + 50 | 99 | 91 |

TABLE XV-continued

| Compound | Formulation | dose rate (ppm) | Observed Efficacy | Expected Efficacy |
|---|---|---|---|---|
| Fenarimol | | 10 + 10 | 52 | 28 |
| | | 2 + 2 | 15 | 9 |
| | | 0.4 + 0.4 | 12 | 0 |
| BP-4 Fenpropimorph | Tankmix | 50 + 50 | 84 | 65 |
| | | 2 + 2 | 19 | 15 |
| | | 0.4 + 0.4 | 13 | 2 |
| BP-4 Flusilazole | Tankmix | 50 + 50 | 100 | 100 |
| | | 2 + 2 | 55 | 28 |
| | | 0.4 + 0.4 | 14 | 5 |
| BP-4 Penconazole | Tankmix | 50 + 50 | 78 | 35 |
| | | 10 + 10 | 19 | 16 |
| | | 2 + 2 | 7 | 3 |
| | | 0.4 + 0.4 | 4 | 0 |
| BP-4 Prochloraz | Tankmix | 50 + 50 | 34 | 25 |
| | | 10 + 10 | 12 | 7 |
| | | 2 + 2 | 4 | 0 |
| | | 0.4 + 0.4 | 0 | 0 |
| BP-4 Pyrifenox | Tankmix | 50 + 50 | 31 | 18 |
| | | 10 + 10 | 15 | 7 |
| | | 2 + 2 | 5 | 0 |
| | | 0.4 + 0.4 | 4 | 0 |
| BP-4 Triadimenol | Tankmix | 50 + 50 | 98 | 98 |
| | | 10 + 10 | 89 | 71 |
| | | 2 + 2 | 39 | 21 |
| | | 0.4 + 0.4 | 10 | 1 |
| BP-4 Spiroxamine | Tankmix | 50 + 50 | 40 | 27 |
| | | 10 + 10 | 11 | 10 |
| | | 2 + 2 | 3 | 0 |

Example 16
Fungicidal Efficacy of the Mixture of BP-4+Other Fungicides (4 Day Residual) Against *Pyrenophora teres* on Barley The tank mixes were obtained from technical material of BP-4 and different formulations of different active ingredients. The active ingredients, the type of formulations, the observed and expected efficacies with different rates are given in Table XVI:

TABLE XVI

| Compound | Formulation | dose rate (ppm) | Observed Efficacy | Expected Efficacy |
|---|---|---|---|---|
| BP-4 | TC 100% | 50 | 11 | |
| | | 10 | 0 | |
| | | 2 | 0 | |
| | | 0.4 | 0 | |
| Cyproconazole | SL 100 g/l | 10 | 1 | |
| | | 2 | 4 | |
| Dinocap | WP 190 g/kg | 50 | 22 | |
| | | 10 | 5 | |
| | | 2 | 0 | |
| | | 0.4 | 0 | |
| Fenarimol | SC 125 g/l | 10 | 4 | |
| | | 2 | 0 | |
| Fenpropimorph | EC 750 g/l | 10 | 3 | |
| | | 2 | 0 | |
| | | 0.4 | 0 | |
| Flusilazole | WP 200 g/kg | 50 | 48 | |
| | | 10 | 26 | |
| | | 2 | 8 | |
| Prochloraz | EC 400 g/l | 10 | 48 | |
| | | 2 | 19 | |
| | | 0.4 | 8 | |
| Pyrifenox | WP 500 g/kg | 50 | 15 | |
| | | 10 | 8 | |
| | | 10 | 1 | |
| | | 2 | 0 | |
| | | 0.4 | 0 | |

TABLE XVI-continued

| Compound | Formulation | dose rate (ppm) | Observed Efficacy | Expected Efficacy |
|---|---|---|---|---|
| Spiroxamine | EC 509 g/l | 50 | 16 | |
| | | 10 | 5 | |
| | | 2 | 3 | |
| | | 0.4 | 0 | |
| BP-4 Cyproconazole | Tankmix | 10 + 10 | 9 | 1 |
| | | 2 + 2 | 10 | 4 |
| BP-4 Dinocap | Tankmix | 50 + 50 | 29 | 31 |
| | | 10 + 10 | 15 | 5 |
| | | 2 + 2 | 5 | 0 |
| | | 0.4 + 0.4 | 9 | 0 |
| BP-4 Fenarimot | Tankmix | 10 + 10 | 6 | 4 |
| | | 2 + 2 | 1 | 0 |
| BP-4 Fenpropimorph | Tankmix | 10 + 10 | 4 | 3 |
| | | 2 + 2 | 5 | 0 |
| | | 0.4 + 0.4 | 5 | 0 |
| BP-4 Flusilazole | Tankmix | 50 + 50 | 70 | 54 |
| | | 10 + 10 | 49 | 26 |
| | | 2 + 2 | 26 | 8 |
| BP-4 Prochloraz | Tankmix | 10 + 10 | 49 | 48 |
| | | 2 + 2 | 30 | 19 |
| | | 0.4 + 0.4 | 19 | 8 |
| BP-4 Pyrifenox | Tankmix | 50 + 50 | 26 | 25 |
| | | 10 + 10 | 10 | 8 |
| BP-4 Triadimefon | Tankmix | 50 + 50 | 29 | 20 |
| | | 10 + 10 | 10 | 5 |
| BP-4 Triadimenol | Tankmix | 50 + 50 | 46 | 21 |
| | | 10 + 10 | 19 | 1 |
| | | 2 + 2 | 3 | 0 |
| | | 0.4 + 0.4 | 1 | 0 |
| BP-4 Spiroxamine | Tankmix | 50 + 50 | 43 | 26 |
| | | 10 + 10 | 24 | 5 |
| | | 2 + 2 | 6 | 3 |
| | | 0.4 + 0.4 | 3 | 0 |

Example 17
Fungicidal Efficacy of the Mixture of Different Benzophenones+Metconazole (2 Day Curative) Against *Blumeria graminis* f. sp. *tritici* on Wheat The tank mixes were obtained from technical material of the benzophenones BP-2 and BP-4 and metconazole. The benzophenones, the type of formulations, the observed and expected efficacies with different rates are given in Table XVII:

TABLE XVII

| Compound | Formulation | dose rate (ppm) | Observed Efficacy | Expected Efficacy |
|---|---|---|---|---|
| BP-2 | EC 100 g/l | 54 | 67 | |
| | | 18 | 25 | |
| | | 6 | 18 | |
| | | 2 | 13 | |
| | | 0.67 | 4 | |
| BP-4 | TC 100% | 54 | 92 | |
| | | 18 | 78 | |
| | | 6 | 42 | |
| | | 2 | 27 | |
| | | 0.67 | 9 | |
| Metconazole | EC 100 g/L | 27 | 40 | |
| | | 9 | 14 | |
| | | 3 | 7 | |
| | | 1 | 2 | |
| | | 0.33 | 0 | |
| BP-2 Metconazole | Tankmix | 27 + 54 | 90 | 80 |
| | | 9 + 18 | 67 | 35 |
| | | 3 + 6 | 46 | 23 |
| | | 1 + 2 | 22 | 12 |
| | | 0.33 + 0.67 | 9 | 4 |
| BP-4 | Tankmix | 27 + 54 | 98 | 95 |

TABLE XVII-continued

| Compound | Formulation | dose rate (ppm) | Observed Efficacy | Expected Efficacy |
| --- | --- | --- | --- | --- |
| Metconazole | | 9 + 18 | 93 | 81 |
| | | 3 + 6 | 49 | 45 |

Example 18

Fungicidal Efficacy of the Mixture of BP-4+AP-4 (1 Day Residual) Against *Uncinula necator* on Vines The tank mixes were obtained from technical material of BP-4 and AP-4. The active ingredients, the type of formulations, the observed and expected efficacies with different rates are given in Table XVIII:

TABLE XVIII

| Compound | Formulation | dose rate (ppm) | Observed Efficacy | Expected Efficacy |
| --- | --- | --- | --- | --- |
| BP-4 | TC 100% | 8 | 42 | |
| | | 4 | 43 | |
| | | 2 | 9 | |
| | | 1 | 28 | |
| | | 0.5 | 21 | |
| | | 0.25 | 0 | |
| AP-4 | TC 100% | 1 | 76 | |
| | | 0.5 | 76 | |
| | | 0.25 | 50 | |
| | | 0.12 | 32 | |
| | | 0.06 | 7 | |
| | | 0.03 | 13 | |
| BP-4 | Tankmix | 8 + 1 | 88 | 86 |
| AP-4 | | 4 + 0.5 | 91 | 87 |
| | | 2 + 0.25 | 85 | 79 |
| | | 1 + 0.12 | 89 | 83 |
| | | 0.5 + 0.06 | 88 | 81 |
| | | 0.25 + 0.03 | 79 | 76 |

Field Tests

Example 19

Fungicidal Efficacy of the Mixture of BP-1+Metconazole in the Field Against the Sugar Beet Disease *Cercospora beticola*

The tank mix was obtained from a SC formulation containing 100 g of BP-1 per liter and a SL formulation containing 60 g of metconazole per liter. The observed and expected efficacies are given in Table XIX

TABLE XIX

| dose rate g/ha | | | |
| --- | --- | --- | --- |
| BP-1 | metconazole | Observed Efficacy | Expected Efficacy |
| 250 | 0 | 42.5 | — |
| 0 | 90 | 58 | — |
| 250 | 90 | 85.4 | 75.9 |

What is claimed is:

1. A fungicidal composition comprising from about 0.1 to 99.9 percent by weight of synergistically effective amounts of (a) at least one benzophenone of formula I

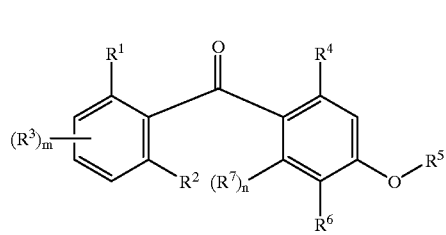

(I)

wherein
R¹ represents a halogen atom, an optionally substituted alkyl, alkanoyloxy or alkoxy group; or a hydroxy group,
R² represents a halogen atom or an optionally substituted alkyl group,
R³ independently represents a halogen atom, an optionally substituted alkyl or alkoxy group or a nitro group;
m is 0 or an integer of 1 to 3;
R⁴ represents a halogen atom, a cyano, carboxy, hydroxy or nitro group or an optionally substituted alkyl, alkoxy, alkenyl, alkylthio, alkylsulphinyl, alkylsulphonyl or amino group;
R⁵ represents an optionally substituted alkyl group;
R⁶ represents a halogen atom or a nitro group, an optionally substituted alkyl, alkoxy, alkenyloxy, alkynyloxy, alkylthio, cycloalkyl, cycloalkyloxy, aryloxy group;
R⁷ independently represents a halogen atom, an optionally substituted alkyl, alkenyl, alkynyl, alkoxy, alkenyloxy, alkynyloxy, cycloalkyl, cycloalkoxy group; and
n is 0 or 1; and
(b) at least one fungicidally active compound selected from a strobilurine derivative having a formula

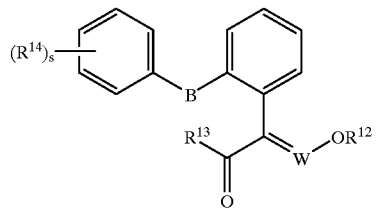

wherein
W represents N or CH;
B represents a —O—, —OCH₂—, a —CH₂O—, a pyrimid-4,6-dioxydiyl group or a group of formula

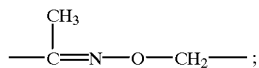

R¹² represents a C₁₋₄ alkyl group;
R¹³ represents a C₁₋₆ alkoxy or a C₁₋₆ alkylamino group;
R¹⁴ represents a hydrogen or halogen atom or a cyano, a C₁₋₄ alkyl or a C₁₋₄ haloalkyl group; and
s is 0, 1 or 2;
wherein the ratio by weight of an (a) to (b) compound is from about 100:1 to 1:100;

together with from about 99.9 to 0.1 percent by weight of a fungicidally acceptable carrier and/or surface active agent therefor.

2. A composition according to claim 1, wherein the benzophenone of the formula I is selected from the group consisting of 6'-butoxy-2,6-dichloro-4',5'-dimethoxy-2'-methylbenzophenone; 2,6-dichloro-4',5'-dimethoxy-6'-(2-fluorobenzyloxy)-2'-methylbenzophenone; 6'-benzyloxy-4',5'-dimethoxy-2,6-dimethyl-2'-methylbenzophenone; 5-bromo-2',6-dimethyl-2,4',5',6'-tetramethoxybenzophenone; and 2,6-dichloro-2'-methyl-4',5',6'-trimethoxybenzophenone.

3. A composition as according to claim 1, wherein the strobilurine derivative of (B) is selected from azoxystrobin, kresoxim-methyl and trifloxystrobin.

4. A composition according to claim 1, wherein the ratio (by weight) of the (a) benzophenone of formula 1 to the (b) fungicidally active compound is from 10:1 to 1:10.

5. A composition according to claim 4, wherein the ratio (by weight) of the (a) benzophenone of formula 1 to the (b) fungicidally active compound is from 5:1 to 1:5.

6. A method of controlling plant diseases or the growth of fungi at a locus which comprises applying to the locus a composition according to claim 1 at a dose rate of the (a) and (b) compound from about 0.01 to 10 kg/ha.

7. A method of controlling plant diseases or the growth of powdery mildew at a locus which comprises applying to the locus a composition of claim 1 at a dose rate of the (a) and (b) compound from about 0.01 to 10 kg/ha.

* * * * *